(12) United States Patent
Hill

(10) Patent No.: US 9,301,963 B2
(45) Date of Patent: Apr. 5, 2016

(54) TREATMENT TOOL AND METHOD OF GRADUAL WITHDRAWAL FROM BEZODIAZEPINE DEPENDENCY

(75) Inventor: Julian Hill, Boulder, CO (US)

(73) Assignee: Julian Hill, Boulder, CO (US)

( * ) Notice: Subject to any disclaimer, the term of this patent is extended or adjusted under 35 U.S.C. 154(b) by 323 days.

(21) Appl. No.: 13/490,358

(22) Filed: Jun. 6, 2012

(65) Prior Publication Data

US 2012/0322794 A1 Dec. 20, 2012

Related U.S. Application Data

(60) Provisional application No. 61/497,690, filed on Jun. 16, 2011.

(51) Int. Cl.
*A61K 31/5513* (2006.01)

(52) U.S. Cl.
CPC .................................. *A61K 31/5513* (2013.01)

(58) Field of Classification Search
None
See application file for complete search history.

(56) References Cited

PUBLICATIONS

Dahar et al., "Food-drug interaction: grapefruit juice augments drug bioavailability—mechanism, extent and relevance," European Journal of Clinical Nutrition (2004) 58, 1-9.*

Ashton, C. Heather "Benzodiazepines: How They Work and How to Withdraw", benzo.org.uk, 2013, 70 pp. Copyright notice dated 1999-2013/printed from the Internet on May 14, 2014.

Harper, James, "The Road Back There is Hope. There is a Solution." http://www.theroadback.org/workbook.aspx, 96 pp, Copyright notice dated 2013/printed from the Internet on May 14, 2014.

"Learning How to Taper off Benzodiazepines and Sleeping Pills Safely", Point of Return, www.pointofreturn.com/benzodiazepine_withdrawal.html, 3 pp, Copyright notice dated 2010/printed from the Internet on May 14, 2014.

"How to Taper off High Potency and or Short Acting Benzodiazepines", www.bcnc.org.uk/water_titration_method.html, 8 pp, printed from the Internet on May 14, 2014.

* cited by examiner

*Primary Examiner* — Sreeni Padmanabhan
*Assistant Examiner* — Jody Karol

(57) ABSTRACT

A treatment tool and method is disclosed for gradual withdrawal from benzodiazepine dependency while reducing or even minimizing withdrawal symptom intensity. An example method includes reducing emotional stress to maintain current neurotransmitter levels, stabilizing a condition with a pre-taper plan, establishing a maximum daily dosage reduction amount of benzodiazepine, based on historical data to prevent symptom escalation, reducing a current dosage of the benzodiazepine by the maximum daily dosage amount on a daily basis for up to about two weeks, and repeating establishing the maximum daily dosage reduction amount and reducing the current dosage until the daily dosage of benzodiazepine reaches zero.

3 Claims, 3 Drawing Sheets

TREATMENT TOOL AND METHOD OF GRADUAL WITHDRAWAL FROM BEZODIAZEPINE DEPENDENCY

PRIORITY CLAIM

This application claims priority to U.S. Provisional Patent Application No. 61/497,690 titled "Method for gradual withdrawal from benzodiazepine dependency" of Julian Hill and filed on Jun. 16, 2011, incorporated herein by reference as though fully set forth herein.

BACKGROUND

Benzodiazepine (or "benzo") is a class of psychoactive drug that enhances the effect of neurotransmitter gamma-aminobutyric acid (GABA), and has a sedative, anti-anxiety, and a muscle relaxant effect. This makes benzodiazepines useful in treating a host of conditions such as but not limited to anxiety, insomnia, muscle spasms, and even to reduce alcohol withdrawal symptoms, in addition to use as a premedication to reduce anxiety associated with medical or dental procedures.

In general, benzodiazepines are safe and effective in the short term (e.g., two weeks of use). However, long-term use has been shown to cause adverse psychological and physical effects, and are prone to physical dependency and issues with withdrawal, known as benzodiazepine withdrawal syndrome (BWS). The long-term use down-regulates the Glutamate/GABA system. Excessive Glutamate levels concurrent with markedly lower GABA levels results in the withdrawal syndrome.

Because many of these symptoms appear identical to accepted psychological diagnoses, the cause of these symptoms is not always correctly diagnosed. Misdiagnosis leaves the "benzo-dependent" patient, not only with a false diagnosis, but without the correct diagnosis for treatment. When left untreated, the withdrawal condition escalates, and may have, for many people, serious physiological effects.

DETAILED DESCRIPTION

Figure 1:
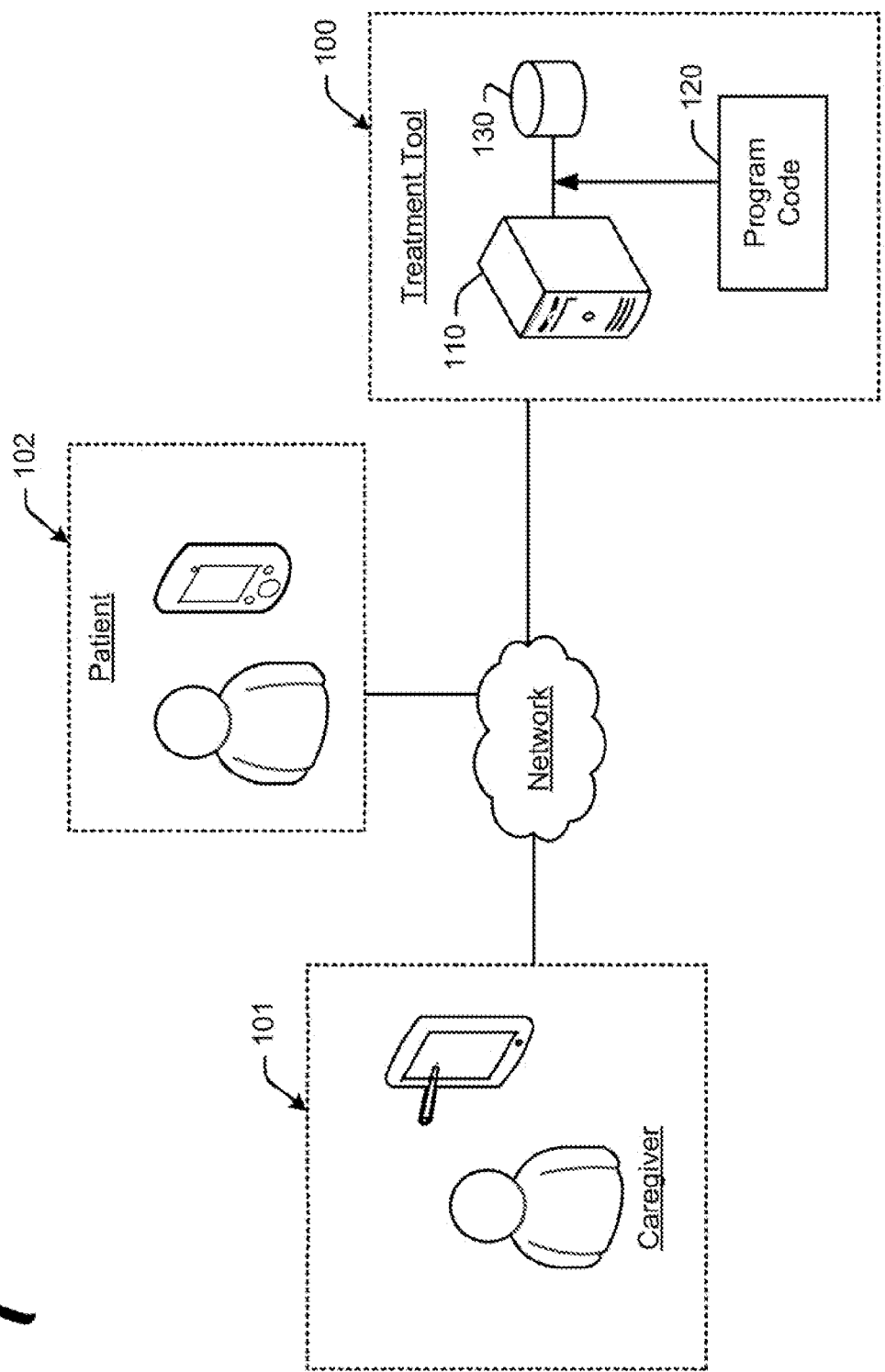
FIG. 1 is a high-level illustration of an example treatment tool for use in assisting gradual withdrawal from benzodiazepine dependency while reducing or even minimizing withdrawal symptom intensity.

A wide range of symptoms may occur with benzodiazepine withdrawal syndrome (BWS), and there is currently no one standard method for diagnosing and treating BWS. A combination of both physiological and emotional symptoms is common. Thus, the symptoms may be difficult to identify, because psychological and neurological problems are traditionally managed by different medical specialties. Emotional or psychological symptoms have received the most attention. However, BWS can also result in physical symptoms only. Physical symptoms often mimic serious neurological diseases. For example, it is not unusual for a patient to receive a false diagnosis of Multiple Sclerosis (MS).

There are many unsubstantiated "treatments." These are based on sometimes false beliefs about the cause and proper treatment. Current "treatments" tend to taper the dosage too quickly for safety, or less often, tapering dosage quickly while anticipating the possibility of seizures. Additional drugs have also been used for "treatment" of BWS, but these simply mask the condition while failing to correct the down-regulation of the Glutamate-GABA system. Down-regulation of the Glutamate-GABA system is recognized as the root-cause of bizarre expressions of benzo-dependency.

One problem with the taper plans is the failure to recognize that 1) recovery is based on the up-regulation of that GABA system, and 2) this up-regulation occurs not in days or in weeks but months and sometimes years. The misconceived treatment may also contribute to the very long time periods needed for proper treatment. By way of illustration, Less-than adequate taper plans appear to cause or allow Protracted Withdrawal Syndrome (PWS), which is the lingering malaise or a lasting feature of the former withdrawal syndrome.

Up-regulation of the GABA system requires months, and sometimes years. Therefore, taper plans employed over weeks or months result in withdrawal of the drug at a rate that far exceeds the individual body's ability to repair itself. No current discontinuation method seeks to address this, and this results in the nervous system being left without drug-support long before it is able to function without drug support.

The procedure disclosed herein reverses Benzodiazepine-dependence by a specific pattern of gradual withdrawal of the drug, without withdrawal symptoms and/or by reducing or even minimizing symptom intensity. Briefly, the procedure identifies a dosage reduction (e.g., an optimal daily or other regular or periodic dosage reduction) for any individual by causing baseline plasma levels to decline exceptionally, evenly, and consistently over any 24 hour period. In an example, the tolerated optimal daily dosage reduction is determined by increasing or decreasing about 0.00125 mg of Clonazepam and 0.125 mg of Diazepam (Valium), or 0.125 mg Chlordiazepoxide (Librium). This procedure reduces, minimizes, or even eliminates the withdrawal syndrome(s) by determining the patient's optimal rate of tapering the dosage of the drug without having to add or substitute anti-convulsant medications for the Benzodiazepine.

Before continuing, it is noted that as used herein, the terms "includes" and "including" mean, but are not limited to, "includes" or "including" and "includes at least" or "including at least." The term "based on" means "based on" and "based at least in part on."

FIG. 1 is a high-level illustration of an example treatment tool 100 for use by a physician or caregiver 101 and/or patient 102 in assisting the patient 102 with gradual withdrawal from benzodiazepine dependency while reducing or even minimizing withdrawal symptom intensity for the patient 102. In an example, the treatment tool 100 may be implemented as in a computing system 110, either as a stand-alone and/or online system described in computer readable instructions 120 and stored on computer readable media 130. When executed by a processor in the computing system 110, the computer readable instructions 120 cause a machine to carry out the techniques described herein. Output may be generated for the user (the physician or caregiver 101 and/or patient 102) for use in assisting the patient 102 gradual withdrawal from benzodiazepine dependency. Example techniques are referenced in the flow diagram shown in FIG. 2.

Figure 2:
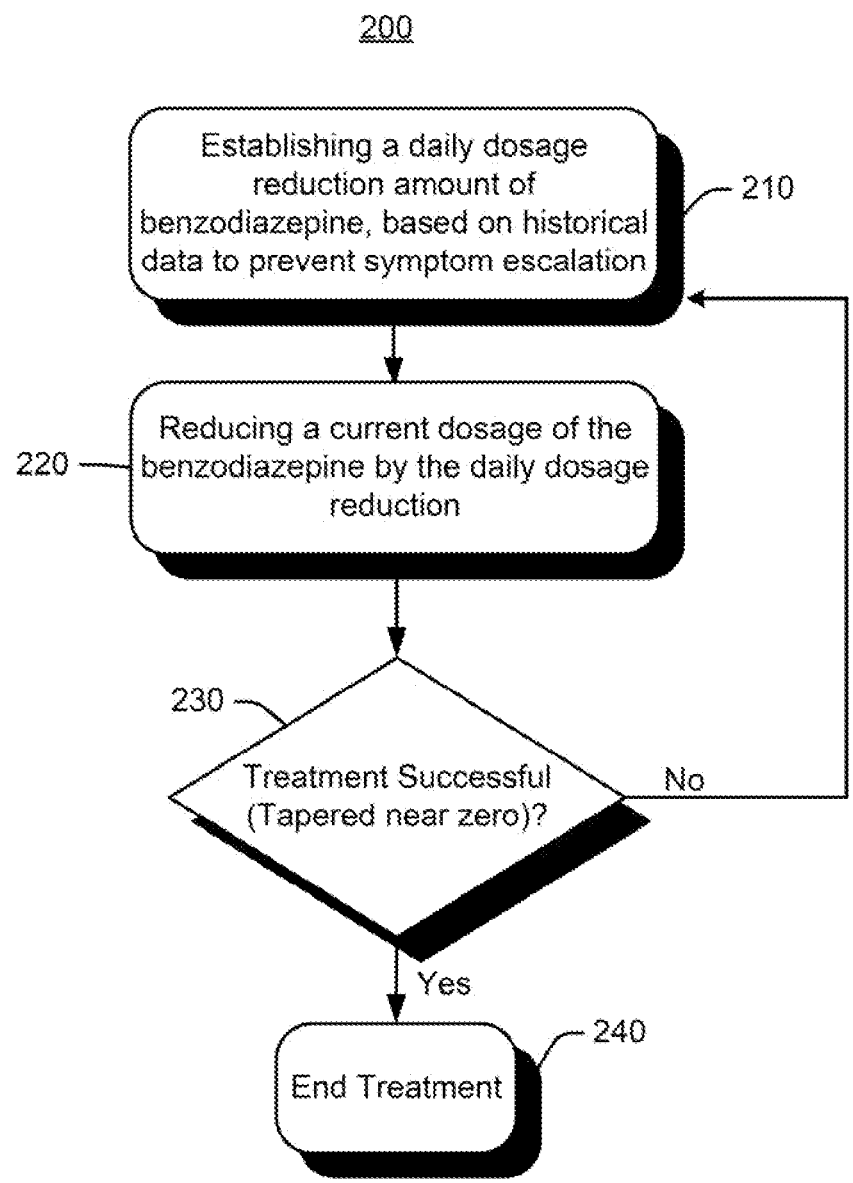
FIG. 2 is a flowchart illustrating example operations which may be implemented as a method for gradual withdrawal from benzodiazepine dependency while reducing or even minimizing withdrawal symptom intensity.

FIG. 2 is a flowchart illustrating example operations which may be implemented as a method for gradual withdrawal from benzodiazepine dependency while reducing or even minimizing withdrawal symptom intensity. An example method 200 of gradual withdrawal from benzodiazepine dependency while reducing withdrawal symptom intensity may include the step 210 of establishing a maximum daily dosage reduction amount of benzodiazepine, based on historical data and careful upward titration to prevent symptom escalation. The method 200 may also include the step 220 of reducing a current dosage of the benzodiazepine by a daily dosage amount, for example a minimum or maximum daily dosage amount on a daily basis (or other periodic or regular basis), e.g., for up to two weeks. It is noted that two weeks is a maximum time that will elapse before a resulting withdrawal syndrome is escalated. Hereafter, that starting rate can be safely increased every three to ten days until symptoms do increase in intensity. When a dosage reduction is found to increase symptoms, the patient should be tapered by the last reduction rate that caused no increase in the withdrawal syndrome. The treatment continues with that found-rate until symptoms once again emerge. This typically occurs at or near the daily dosage of 5.0 mg Diazepam or 0.25 mg of Clonazepam, or 12.5 mg Chlordiazepoxide.

At this point of symptom emergence, the taper continues with smaller and smaller reductions, continuing to taper with these smaller dosage reductions until the dosage is at or near zero milligrams. In an example, reductions continue to exactly zero milligrams). By way of illustration, a 0.01 mg reduction results in 0.09 mg, 0.08 mg, 0.07 mg, and so forth to 0.02 mg, 0.01 mg, and then arriving at 0.0 mg.

This is illustrated by the flowchart diagram in FIG. 2, where a determination 230 is made whether the treatment has been successful, and if yes, then the treatment may be ended at 240. Otherwise, steps 210 and 220 may be repeated by establishing a daily dosage reduction amount and reducing the current dosage until the daily dosage of benzodiazepine reaches zero where little or no post withdrawal syndrome remain.

The techniques shown in FIG. 2 are described in more detail below. While these techniques may be implemented in a computer environment such as the system shown in FIG. 1, the treatment method may also be carried out by a patient, caregiver, or physician who is trained in this benzodiazepine discontinuation protocol. The use of today's detoxification or rehabilitation facilities is unnecessary and may even be harmful or irrelevant to the benzo-dependency issue, for valid and effective and humane treatment of the iatrogenic benzodiazeoine-dependent patient.

The treatment tool may be used to implement a pattern of adjusting dosages to more closely match and address the nervous system's changing need for a GABA agonist. The method described herein seeks to very closely match the rate of withdrawal to the rate of nervous system repair.

In an example, the treatment tool may first seek to help stabilize the patient's condition with a pre-taper plan. The goal of the pre-taper plan is to cause levels of the drug in the blood to remain as close as possible to the same amount over any 24 hour period. In patients who are metabolizing the drug too quickly, maintaining these required even levels may be facilitated by dividing the total day's dose into two to four divided doses. This approach prevents the graphed peaks and troughs in drug levels, which are responsible for the waxing and waning of symptom levels. Other approaches may also be implemented when the tapered drug is one that is metabolized by any of the CYP 450 enzymes. Lorazepam, Oxazepam, and Temazepam are benzodiazepines that are not metabolized by the CYP 450 enzyme pathways.

As pre-taper work, the taper-environment is addressed. Foods, drugs, and even exposure to cigarette smoke and charcoal-barbecued foods are identified and removed from the taper environment. Many antidepressants inhibit the benzodiazepine metabolizing CYP 450 enzymes and so will increase the average amount of benzodiazepine to beyond the amount expected to be present in the body. A premature discontinuation of the taper may cause a too large drop in benzo levels and result in a possibly severe resurgence of symptom levels. These are to be used until the benzodiazepine is completely tapered. These efforts remove conditions that can increase (or less often, decrease) the CYP 450 enzyme activity in the patient. In addition, the patient is advised to avoid emotional stress, because stress can increase levels of neurotransmitters that are inadequately modulated by the down-regulated GABA activity. This pre-taper phase typically lasts for about two weeks, depending on the patient's response.

Next, the treatment tool helps the physician (or caregiver or patient) determine if the current drug (benzodiazepine) has an inadequate half-life, as evidenced by inter-dose withdrawal symptoms. If so, the dependent patient may be crossed over to a longer half-life drug. North American physicians tend to favor Clonazepam, which has a relatively long half-life. Clonazepam also has no active metabolites, such as Valium which has one inactive metabolite and two active metabolites (Temazepan and Oxazepam). It is the presence of active metabolites that cause concern for most physicians in the USA and Canada. There is also a concern that these metabolites may accumulate in fatty tissue and cause other, unspecified problems.

It is noted that clearance of the drug is often faster with continued use. This phenomenon, referred to as inter-dose withdrawal, explains why withdrawal symptoms tend to occur sooner and sooner after the last scheduled dose has been missed. It is also noted that the drug's duration of action is noticeably shorter than the expected half-life. For this reason, even Clonazepam and Diazepam may not remain in the body long enough to prevent a resurgence of withdrawal symptoms, interdose withdrawal symptoms, before the next scheduled dose.

Based on reports from actual patient cases, there is a very narrow dosage interval that is acceptable and which causes no symptom escalation. The treating physician can use a minimum number as a starting reduction, and it should prevent symptom escalation. That number may be below the standard reduction of 0.05 mg and a reduction of 0.01 mg Diazepam or equivalent may be more appropriate. Degree of symptoms indicates time to use the smaller numbers. By making the dosage cut at regular intervals (e.g., every day), and by doing this for a predetermined time (e.g., two weeks), the dosage cut can be monitored at maintained at acceptable levels. Then, that dosage cut can be increased by another known amount, wait for the predetermined time (e.g., three days to two weeks referred to as the patient's determined "lag" time), and if all is well with the patient, another increase can be employed. When an increased cut causes a rise in symptoms, a previous acceptable dosage cut can be used again.

This pattern of increasing the daily dosage cuts by very small increments allows finding the optimal daily cut for any individual. In an example, an optimum dosage can be found in the range of +/−0.00125 mg of Clonazepam and +/−0.0125 mg of Diazepam. The determined daily dosage reduction allows the benzo-dependent patient to continue at this rate until the daily dose falls close to 5.0 mg diazepam or 0.25 mg of clonazepam. At this or near dosage, the daily reductions usually must be made smaller.

An increased level of symptoms typically indicates that it is time to change the dosage. Thus, the daily reductions can be made by following the reverse of the increased dosages to find the appropriate dose. This process continues to cause a very slow, mild, and very even decline in the drug levels, and thus causes no symptoms or minimal symptoms for the patient, until the total dosage approaches or reaches zero milligrams. At this point, the patient should have no further need of the drug, and thus faces no post withdrawal syndrome as experienced using other methods.

In an example, total doses may be 5.0 mg Diazepam and 0.25 mg Clonazepam, but the accustomed daily reduction can be changed. When the daily dosage falls to 5.0 mg Diazepam or 0.25 mg Clonazepam, or 12.5 mg Chlordiazepoxide, the accustomed daily reduction number may have to be changed to a smaller number. This decision is symptom-driven. A smaller reduction may be needed, as determined by making the daily cuts smaller in the reverse order of having made the cuts bigger. That is, the daily reductions are implemented in a reverse order, as smaller and smaller sized cuts. This change may be implemented just once or many times, as determined based on patient symptoms.

The taper causes a dosage decline in a consistent and even manner, and no Post Withdrawal Syndrome (PWS) follows the discontinuation of the drug because the GABA receptors have had small changes that signal the need for repair of the system. The changes are not large enough to cause a cascade of worsening symptoms. And no taper-induced hypertension has emerged which might otherwise cause heart damage.

Determining the optimal daily dosage reduction usually takes about two to three weeks. Once this dosage amount is determined, and the patient has learned how to measure and record the numbers, the process can continue at home for much of the remaining taper process. When total daily dosage of 5.0 mg Diazepam and 0.25 mg Clonazepam or 12.5 mg Chlordiazepoxide is reached, the daily reductions may be reassessed.

It is noted, as a cautionary measure, that the syndrome improves as the dosages are reduced in this manner. When the patient feels well while using this method, the patient may want to stop the process. However, the need for some amount of the drug may remain—it is merely being managed adequately by the still-present, but small amount of the Benzodiazepine. The patient should be advised not to stop the process until the dosage is very near or zero milligrams. Once the patient has reached a zero dosage, the patient's physiological systems have had time to change and GABA receptors have returned to adequate function for normal life-circumstances or stressors.

It is also noted that if the patient's coping skills had been inadequate before initiating the drug and the drug had masked that deficit, this very mild and consistent withdrawal allows time for the patient to gradually learn or relearn those skills. Psycho-therapy may have been hindered while the benzodiazepine was masking the lack of skills. With very mild withdrawal, the therapist can take advantage of the gradual return to normal GABA function. The drug is withdrawn at a schedule in keeping with repair of the physical abnormality of the Glutamate-GABA system. This mild and even recovery provides the patient an opportunity to match the increasing absence of the drug to the structured development of the formerly lacking coping skills.

The treatment tool described herein implements a method of progressive dosage changes in response to emergence of symptom signals. The method accounts for the effects of the internal and external taper environment and respects the effects of the natural clearance of the drugs.

As such, the method can be described as a multifaceted procedure that allows a patient to safely discontinue use of any benzodiazepine drug, by determining changing dosage reductions that are safe for the patient. The procedure avoids seizure activity during the discontinuation process, limits or altogether eliminates symptoms.

The treatment tool may be used in conjunction with a specific delivery media, as described in the examples below, to ensure accurate dosage reductions to enable a benzodiazepine-dependent patient to determine a sequence of dosage reductions that are unique to the patient, and to the patient's changing internal taper-environment. The treatment tool and methods described herein ensures that the patient's Glutamate/GABA system is up-regulated to normal function by the time the procedure is completed. Thus, the procedure does not cause any deleterious health consequences from discontinuing the benzodiazepine.

EXAMPLES

In this example, the patient's condition was first stabilized by adding small amounts of the drug until the benefit no longer increases. This dosing was used for up to about two weeks. It should be noted that if there was sudden and total discontinuation of the drug, the patient may feel no problems at all for two weeks. This period is referred to as the "benzo latency period (BLP)." The time interval is specific to each patient. During the taper itself, the time elapsed between making a dosage change and feeling resulting symptoms is called the "benzo-symptom lag time." It is this lag time that makes necessary waiting for three to ten days before initiating a larger dosage cut.

The patient's drugs, herbs, and foods were also checked for induction of CYP450 enzymes that metabolize the benzo. This prevents using substances that would cause a "too quick" benzo metabolism and prevent the mild and even and consistent fall in blood levels which allows reduced or even minimal withdrawal symptoms.

Next, the day's dose was divided into two to three evenly spaced doses, and the patient took these partial doses at even intervals during a 24 hour period. Tapering began with a reduction of 0.05 mg for Diazepam, 0.0025 mg Clonazepam, and 0.125 mg Chlordiazepam, and 0.0025 mg for Alprazolam. These, with the notable exception of Alprazolam, are the most common long half-life benzos. If there is no inter-dose withdrawal when using Alprazolam, then Alprazolam may be also used as a direct taper. The correct solvent for Alprazolam is ethanol.

It is noted that suspensions have not been found to be suitable. All taper benzos described herein are in a liquid in which the benzo is soluble. For example, a fat/water emulsion such as 4% fat homogenized milk is suitable for Diazepam and Clonazepam. Milk is a fat/water emulsion offering the advantages of both a solution and the kind of suspension created by homogenization.

Ethanol can be used to make a solution of Diazepam. In an example, an amount of ethanol to create a useable solution is about 0.19 mL ethanol per 1.0 mg of Diazepam. Water can be added to the ethanol solution to product the desired strength.

It is noted that any dosage can be measured, because the liquid that contains it in the solution can be made at any strength. In an example, the prescription liquid diazepam is dispensed as 1:1 or 2.5. However, it can be diluted to any weaker strength to yield the desired number of milligrams in a convenient number of milliliters. In an example, a good useable strength of 40.0 mL per 1.0 mg is used for Alprazolam and Clonazepam; and 10.0 mL per 1.0 mg may be used for Diazepam.

When it is known how much time will elapse between making a dosage reduction and feeling the resulting change in symptoms, this is the time to test the new dosage before making the reduction larger.

The procedure begins with a daily reduction of 0.05 mg Diazepam, and when the dosage cut is found to cause no symptoms, the dosage cut was gradually increased by from 0.06 to 0.1 mg daily, and followed by the symptom lag time that was appropriate for the patient. It has been found that a dosage cut of 0.1 mg Diazepam is often the limit. When this is achieved, the dosage was cut by additional 0.1 mg daily until symptoms emerged again. This typically occurs at about a 5.0 mg Diazepam daily dosage. At this point, the dosage cuts are reversed by using progressively smaller cuts. This can be repeated as desired until zero milligrams of the drug is reached as a daily dosage.

A significant difference between the taper method described herein, and other methods for reducing dependency, is the use of a liquid delivery, beginning with a reduction so small that the dosage reduction does not cause withdrawal symptoms, then increasing the daily reduction until the patient's symptoms increase. At that point, the last sized reduction that caused no increase in symptoms is used again. Eventually, at a dose near 5.0 mg Diazepam or its equivalent, the patient's symptoms may reappear. At this point, the size of the reductions can be made progressively smaller. As the patient approaches zero milligrams of the drug, the rate of reduction can be slowed. This represents a reverse of the beginning of the taper.

It is noted that the technique may implement a crossover to an equivalent amount of Diazepam, Clonazepam, or Chlordiazepoxide. The substituted drug doses are divided into two to four substantially equal sized divided doses in each 24 hour period.

It is further noted that after the strengths and reduction amounts are determined, the daily measuring and dosing can be done by the patient or caregiver at the patient's home or other setting which is more convenient for the patient than at a physician's office or clinic. Some instruction in using oral syringes in a safe and quiet setting may be provided to enable learning the technique without worry to the caregiver or causing tension in the patient. Practice enables most patients to implement the procedure and record results. The record may be delivered to the monitoring physician at each visit.

The techniques described herein have been used with many patients. Many of these patients were coming off of a large dosage of benzodiazepine. Some of these dosages were more than 4.0 mg Clonazepam, and at least one patient was on 8.0 mg Clonazepam. Every patient has found his or her best taper rate and recovered to return to normal life activities following the treatment method described herein. Treatments relying on reductions and scheduled intervals expressed as percentages or as a standard number tend to fail. These older techniques have not sought to find acceptable dosage reductions that do not exceed the individual body's ability to re-up-regulate the damaged Glutamate-GABA system. Thus, these techniques tend to cause unnecessary suffering and pave the way for unwanted physiological changes. But each of the patients using the method described herein, either before the withdrawal syndrome emerged, or shortly after the patient felt the beginning of their withdrawal syndromes gradually fade in intensity and fall to zero when the taper was complete. The patients did not report any adverse symptom escalation. All patients experienced different but gradual lessening of symptoms as their taper progressed.

According to the protocol described herein, the dosage-cut is determined by first employing a cut so small that it does not increase the withdrawal symptom level of any physically benzo-dependent person. Then subsequent small increases in dosage cuts are made until the maximum dosage cut that causes no symptoms is known for that patient. In this way, the body acclimates to the higher dosage reduction without causing illness. In addition, a true solute/solvent solution is used to cause the most homogenous dispersion of benzo in its appropriate solvent. Example solvents for some benzodiazepines are fat, ethyl alcohol, and water. The use of a solution as opposed to a suspension or mixture allows the extreme accuracy needed in measuring the desired micro-cuts. Suspensions allow the crystalline benzo to precipitate thus causing a non-homogenous liquid delivery liquid and so measurements of these are inaccurate.

Figure 3:
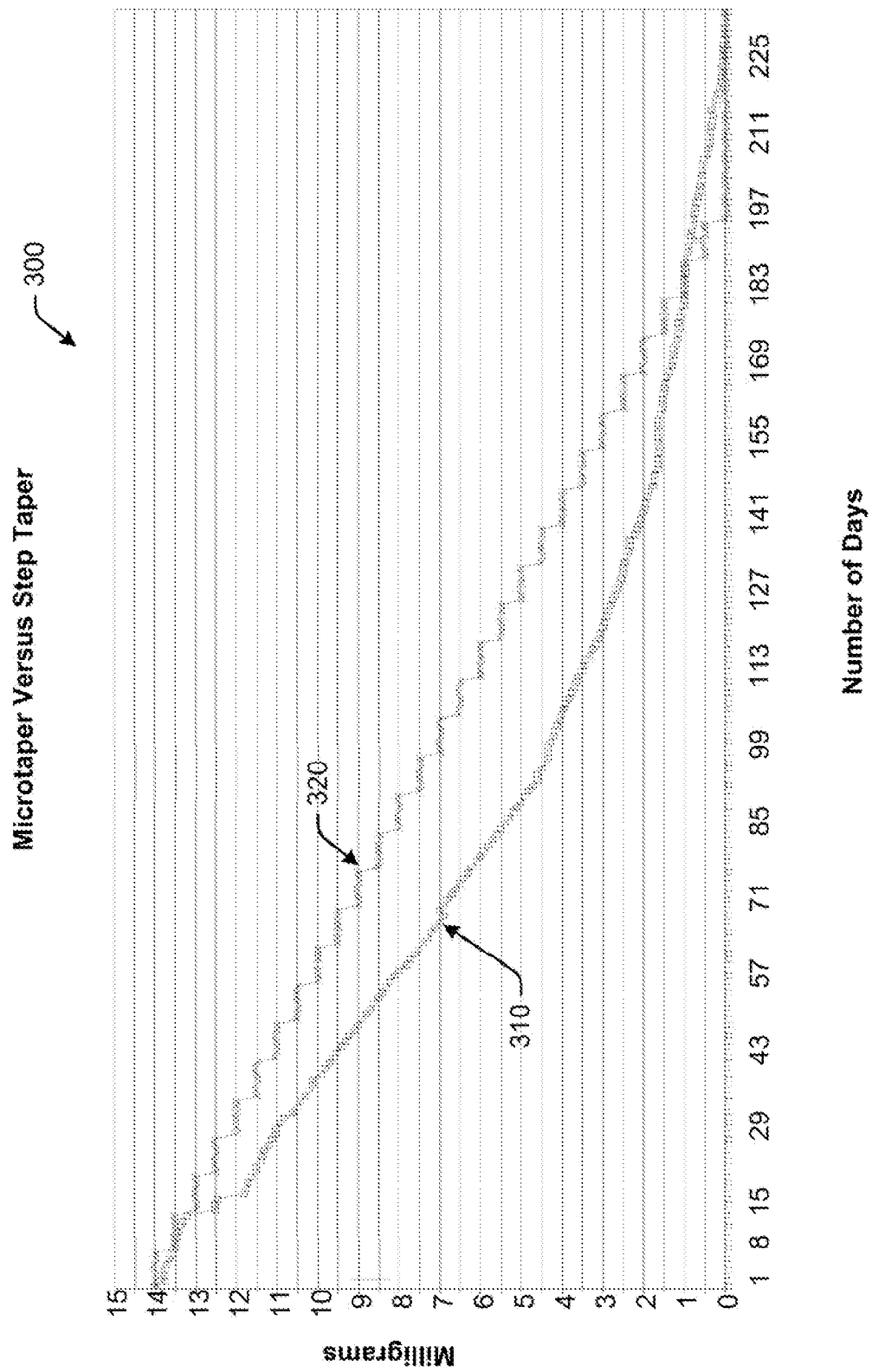
FIG. 3 is a plot showing actual results of an example method described herein compared with a step taper method.

FIG. 3 is a plot 300 illustrating results of an example method described herein compared with a step taper method. The line 320 shows actual dosage descent for a patient who used this procedure. The line 320 is an illustration of another taper procedure used to treat a patient on the same starting dose (14.0 mg) of Diazepam. Sharp drops as in the vertical segments of the line 320 shows after "steps" are always accompanied by hard-to-endure benzodiazepine withdrawal symptoms. As can be seen, the line 310 is virtually free of harsh drops. This represents no symptom escalation from dosage reduction.

The line 320 also indicates that the Step-Taper was abruptly halted at 0.5 mg Diazepam. This sudden cessation together with the brutal "steps" causes the feared post withdrawal syndrome. Cases indicate that this procedure, illustrated by the line 310, both eliminates the post withdrawal syndrome and prevents the symptom escalation as the taper progresses.

It is noted that the examples shown and described are provided for purposes of illustration and are not intended to be limiting. Still other examples are also contemplated.

The invention claimed is:

1. A method of gradual withdrawal from diazepam dependency while reducing withdrawal symptom intensity, comprising:
   (1) reducing a current dosage of diazepam by 0.01 mg per day for 10 to 14 days;
   (2) increasing said daily dosage reduction by 0.01 mg from 0.01 mg to 0.02 mg per day of diazepam for a cycle of 10 to 14 days;
   (3) repeating said 0.01 mg per day increase in daily dosage reduction per cycle of 10 to 14 days until the daily dosage of diazepam reaches 0.0 mg;
   wherein a liquid formulation of diazepam is used and wherein the maximum daily dosage reduction of diazepam is 0.1 mg per day to 0.17 mg per day; and wherein at any time during treatment if a decreased dosage causes a rise in symptom intensity, returning to the previous acceptable dosage reduction and maintaining said dosage reduction until withdrawal symptoms increase or the daily dosage of diazepam reaches 0.0 mg.

2. The method of claim 1, further comprising stabilizing a condition with a pre-taper plan.

3. The method of claim 2, wherein the pre-taper plan includes removing any foods, drugs, and other environmental exposure affecting CYP450 enzyme activity that metabolizes the benzodiazepine.

* * * * *